United States Patent [19]

Ishimura et al.

[11] Patent Number: 4,727,030

[45] Date of Patent: Feb. 23, 1988

[54] PREPARATION OF POROUS POLYVINYL ALCOHOL GEL CONTAINING AN IMMOBILIZED ENZYME

[75] Inventors: Fumihiro Ishimura; Koji Murata, both of Shizuoka; Suong-Hyu Hyon; Yoshito Ikada, both of Kyoto, all of Japan

[73] Assignees: Toyo Jozo Co., Ltd.; Biomaterials Universe, Inc., both of Japan

[21] Appl. No.: 791,274

[22] Filed: Oct. 25, 1985

[30] Foreign Application Priority Data

Oct. 26, 1984 [JP] Japan .............................. 59-223829

[51] Int. Cl.⁴ ..................... C12N 11/04; C12N 11/14; C12N 11/02; C12N 11/08
[52] U.S. Cl. ................................. 435/182; 435/176; 435/177; 435/180
[58] Field of Search ............... 435/174, 176, 177, 178, 435/182

[56] References Cited

U.S. PATENT DOCUMENTS

| | | | |
|---|---|---|---|
| 4,148,689 | 4/1979 | Hino et al. | 435/182 |
| 4,272,617 | 6/1981 | Kaetsu et al. | 435/182 |
| 4,604,354 | 8/1986 | Katz et al. | 435/177 X |
| 4,617,271 | 10/1986 | Nambu | 435/182 |
| 4,634,672 | 1/1987 | Baumgarten et al. | 435/182 |

FOREIGN PATENT DOCUMENTS 0107181 6/1983 Japan ................... 435/182

*Primary Examiner*—David M. Naff
*Attorney, Agent, or Firm*—Sughrue, Mion, Zinn Macpeak & Seas

[57] ABSTRACT

A porous gel containing an immobilized enzyme is prepared by mixing an aqueous solution of polyvinyl alcohol having a saponification degree of not lower than 95 mol% and an average polymerization degree of not lower than 1,000, with an enzyme or enzyme-producing cell, and activated carbon powder, pouring the mixture into a container of any desired form, gelating and molding the mixture by dehydrating it up to a dehydration ratio of not lower than 50%, immersing the resulting molding in water, and drying the immersed molding. Preferably, dehydrating is by leaving the mixture to stand at room temperature or a temperature of from 30° C. to 40° C. The enzyme or enzyme-producing cell may be mixed with or adsorbed on an inorganic or organic carrier. The dried molding may be granulated.

12 Claims, No Drawings

PREPARATION OF POROUS POLYVINYL ALCOHOL GEL CONTAINING AN IMMOBILIZED ENZYME

FIELD OF THE INVENTION

The present invention relates to a process for the preparation of firm and porous polyvinyl alcohol (PVA)-gel containing an enzyme or cells of a microorganism, plant or animal immobilized thereon.

BACKGROUND OF THE INVENTION

Recently, with the significant progress in the technique of utilizing microorganisms or enzymes produced therefrom, numerous processes for immobilizing enzymes or microbial cells have been proposed and many inventions have been made to utilize enzyme reactions effectively. However, only a few of them have succeeded in industrialization. That is, besides the problem of manufacturing cost, many of the techniques hitherto developed involve various disadvantages, e.g., severe conditions are required to immobilize enzymes or microbial cells, that there is a problem that the bioactivities of the enzymes or microbial cells are reduced upon immobilization using polyfunctional reagents; there is a problem in the physical tolerance of immobilized enzymes or microbial cells whose low mechanical strength cannot tolerate industrial use and may cause clogging of pores due to the deformation by liquid pressure of the substrate; and there is a problem in the safety of immobilized enzymes or microbial cells, or their products, which are obtained by using harmful monomers, cross linking agents or the like for the immobilization.

Hitherto, various processes for immobilizing enzymes or microbial cells by means of PVA are known. For instance:

(1) A process for immobilizing enzymes by gelating at low temperatures an aqueous solution containing PVA and an enzyme has been proposed (Japanese Patent Application (OPI) No. 52276/75). (The term "OPI" as used herein means a "published unexamined Japanese Patent application".) The gel obtained by this process, however, does not show any elasticity and its mechanical strength is very low. Moreover, only a weak or soft gel is obtained when air-drying is effected after the solidification and fusion, and only a fragile gel hardly showing any elasticity is obtained even when dehydration under reduced pressure is carried out or dehydration is effected over a long period of time, instead of the air-drying. Therefore, this process is not an industrially valuable process.

(2) A process for immobilizing enzymes or microbial cells by instantly gelating an aqeous solution of enzymes or microbial cells by adding thereto an aqueous solution of boric acid or borax has been proposed (Japanese Patent Publication No. 51552/80, Japanese Patent Application (OPI) No. 135293/79). The gel obtained by this process, however, is weak and hardly molded.

(3) A process of immobilization by adding an acid to a suspension containing PVA, tetraethyl silicate and microbial cells and air-drying the mixture has also been proposed (U.S. Pat. No. 4,148,689). The membrane obtained, however, is also weak. Even when freezing and drying are effected after the addition of acid, the membrane produced is reduced in its mechanical strength and is almost incapable of being molded.

(4) A process for immobilizing living microbial cells in a gel by drying an aqueous suspension containing an aqueous PVA solution, living microbial cells and a clay mineral at a temperature of from $-6°$ to $+40°$ C. to dehydrate it until a gel of prescribed moisture content is formed, has also been proposed (Japanese Patent Application (OPI) No. 138390/82). The immobilized microbial cells obtained by this process, however, are still weak and fragile, and does not reach an industrially available strength. In addition, they have a defect in that their activity per volume is lowered because of the clay mineral is employed in a large amount and accordingly the volume of a reactor for the enzyme reaction increases significantly.

(5) A process for immobilizing microbial cells in a gel by freezing and molding an aqueous suspension containing an aqueous PVA solution, living microbial cells and a clay mineral, and then vacuum-drying the molded frozen suspension without melting it, i.e., by so-called freeze-drying, has been proposed (No. EP-60052-A and Canadian Pat. No. 1180670). Likewise, a process for immobilizing microbial cells in a gel by freezing and molding an aqueous suspension containing an aqueous solution and living microbial cells and thereafter immobilizing the cells in the gel formed without causing melting, has been proposed (No. EP-60052-A and Canadian Pat. No. 1180670). The immobilized microbial cells obtained by these processes are relatively firm and reveal a high bioactivity. However, they are disadvantageous in that, since they are obtainable only in a voluminous form and their volume increases further as a large amount of the clay mineral is incorporated, the activity of micobial cells per unit volume decreases and the volume of a reactor increases significantly as they are utilized in enzyme reactions. In these processes, the suspension is frozen and molded in a plate mold having fine pores and then freeze-dried, without being molten, to give a plate molded gel. However, there is a defect in that fine granulation cannot be effected at the stage where the suspension is frozen and molded because the suspension will be defrozen if granulation is tried. Further, there is a defect in that the high cost of the equipment and energy (power for dehydration) is necessary for freeze-drying, as a large amount of moisture is removed by the freeze-drying.

Generally speaking, molding of a mixture of aqueous PVA solution and an enzyme or microbial cells is effected by a process wherein the molding is effected after the PVA gel is formed or by a process wherein the molding is effected by pouring the mixture into a container or mold for molding of any desired form before the PVA gel is formed. In the molding process effected after the formation of PVA gel, it is difficult to obtain a molding of desired form due to the tackiness of the gel formed, and moreover it is impossible to obtain an immobilized enzyme or microbial cell having an industrially sufficient strength (the processes (1) to (4) mentioned above). Also in the molding process effected before the formation of PVA gel wherein a mixture of aqueous PVA solution and living microbial cells is poured into a container or mold for molding of any desired form, frozen and freeze-dried, it is difficult to obtain granular immobilized microbial cells having a diameter of 1 to 3 mm which are used industrially for enzyme reactions, not to speak of the enormous costs of the equipment and energy for the freeze-drying.

SUMMARY OF THE INVENTION

An object of the present invention is to provide a process for the preparation of immobilized enzymes or enzyme-producing cells having a high mechanical strength and being tolerant of industrial use.

Another object of the present invention is to provide a process for the preparation of immobilized enzymes or enzyme-producing cells which are porous, excellent in water permeability, significantly small in volume compared with immobilized cells obtained by a freeze-drying method, and are valuable as a reaction catalyst for enzyme reactions.

Still another object of the present invention is to provide a process for the preparation of immobilized enzymes or enzyme-producing cells which can be freely granulated at the stage where a mixture of an aqueous PVA solution and an enzyme or cell is gelated by drying and molded.

Yet another object of the present invention is to provide a process for the preparation of immobilized enzymes or enzyme-producing cells which does not require freeze-drying and accordingly has a much reduced cost for equipment and energy (power for dehydration).

With a view to overcoming the defects as mentioned above of the known techniques, the inventors of the present invention have made various investigations. As a result of the investigations, it has been found that the immobilized enzymes or enzyme-producing cells obtained by uniformly mixing an aqueous PVA solution; an enzyme liquor, cells or a suspenion of cells; and activated carbon powder with one another, spontaneously drying or air-drying the mixture in a container of any desired form, until the dehydration ratio of said mixture reaches a value higher than 50%, to make PVA a half-dried gel and molding said mixture by the gelation, immersing the molding in water so that it contains moisture uniformly, and drying the mold, are porous and excellent in water permeability, still have an extremely high mechanical strength, and that the volume of said immobilized enzymes or cells is very small as compared with that of immobilized microbial cells obtained by the known process (5) described above. As a result, the volume per unit enzyme activity, i.e., the specific volume, is small.

It has also been found that with the above mixture, moldings obtained by half-dry gelation, having suitable strength and elasticity and being free from tackiness, can be granulated freely. That is, molding can be effected more easily as compared with the above molding process (5).

Further, it has been found that with the above mixture immobilization can be performed economically in an industrial scale since the gelation is effected by spontaneous drying or air drying, and not by freeze-drying which requires high cost equipment and energy (power for dehydration).

Thus, the present invention provides a process for the preparation of firm and porous gel containing immobilized enyzme or enzyme-producing cell, comprising (A) mixing an aqueous solution of PVA having a saponification degree of not lower than 95 mol% and an average polymerization degree of not lower than 1,000, with an enzyme or encyme-producing cell, and activated carbon powder, (B) pouring the mixture into a container of any desired form, (C) gelating and molding the mixture by dehydrating it up to a dehydration ratio of higher than 50%, (D) immersing the resulting molding in water, and drying the immersed molding.

DETAILED DESCRIPTION OF THE INVENTION

The PVA used in the present invention is one having a saponification degree of now lower than 95 mol%, preferably, not lower than 97 mol%, so that only a weak or fragile gel containing an immobilized enzyme is obtained. The PVA used in the present invention has a polymerization degree of not lower than 1,000, preferably, not lower than 1,500, by average viscosity. With the lowering of the polymerization degree of PVA, the mechanical strength of the gel containing the immobilized enzyme obtained is lowered. It is suitable to use a commercially available PVA having a high polymerization degree of about 1,700 to 2,600.

According to the present invention, an aqueous PVA solution having a concentration of 5 to 30 w/w%, preferably 10 to 20 w/w% is first prepared. If the concentration is lower than 5 w/w%, the mechanical strength of the gel containing the enzyme obtained is lowered. On the other hand, if the concentration is higher than 30 w/w%, the viscosity of aqueous PVA solution increases and preparation of the aqueous PVA solution becomes difficult. Usually, the preparation of aqueous PVA solution is effected by dissolving PVA under heating.

Hereinafter "enzyme" shall mean an enzyme or an enzyme-producing cell. The enzyme may be used alone or in the form of a solution or suspension in an aqueous medium, such as water or a buffer solution.

The above enzyme may be one which is partially purified or one which is sufficiently purified. That is, the enzyme may be of any purification degree. Further, the enzyme may be in the form adsorbed physically on an inorganic or organic carrier or in the form admixed with such carrier.

The term "carrier" as used herein refers to a water-insoluble inorganic or organic substance which does not inactivate the enzyme or cell and, as the case may be, adsorbs the enzyme or cells. Examples of such known organic high-molecular polymers include Sephadex, agarose, cellulose, etc.

The enzyme, which is used in the present invention includes, (a) an enzyme; (b) an admixture of enzyme and an inorganic or organic carrier; (c) an enzyme adsorbed on an inorganic or organic carrier; a suspension of the above (b) or (c); (d) an enzyme solution or suspension; (e) an admixture of enzyme solution or suspension and an inorganic or organic carrier; (f) an enzyme solution or suspension adsorbed on an inorganic or organic carrier; or a suspension of the above (e) or (f) is employed. Alternatively, a living cell, a dried cell or a broken cell; (g) an admixture of such cell and an inorganic or organic carrier; (h) a such cell adsorbed on an inorganic or organic carrier; a suspension of a living cell, a dried cell or a broken cell; or a suspension of the above (g) or (h) is employed.

In the present invention various known enzymes derived from animals, plants or microorganisms can be employed. However, enzymes derived from microorganisms are suitably used. Examples of the enzymes include glucose isomerase, fumarase, aspartase, amylase, glucoamylase, trypsin, chymotrypsin, pepsin, papain, pancreatin, aminoacylase, penicillin acylase, cephalosporin acylase, nuclease, ribonuclease, ficin, catalase, galactosidase, ATP-deaminase, L-glutamic acid dehydrogenase, phosphatase, tyrosinase, invertase, flavokinase, streptokinase; apyrase, ATP-creatin phosphoric acid transferase, pectinase, carboxypeptidase, L-asparaginase, maltase, lactase, urease, tannase, lipase, melibiase, aldolase, cellulase, anthocyanase, naringinase, hesperidinase, D-amino acid oxidase, glucose oxidase, L-phenylalanine ammonia lyase, an enzyme synthesizing aspartame from L-aspartic acid and L-phenylalanine methyl ester, and the like.

Besides those described above, there can be mentioned also the known enzymes described in "Enzyme Handbook" edited by Bunji Naruo and Nobuo Tamiya (Dec. 1, 1982, Asakura Shoten).

The above enzyme-producing microbial cell may belong to bacteria, actinomycetes, mould or yeast, as far as it is a microorganism which produces an enzyme as mentioned above. The microbial cell may be either living one or dried one, or also one broken partially or completely, as far as it has enzyme activity. Further, such microbial cell may be in the form physically adsorbed on a water-insoluble inorganic or organic carrier or in the form admixed with such carrier.

As enzyme-producing cells various animal and plant cells can also be employed. Examples of such animal cells include Namalva cells producing α-interferon, monoclonal antibody-producing cells obtained ley cell fusion between a murine spleen cell sensitized with a specific antigen and a P3/N51/1-Ag4-1 or P3X63Ag8 cell, etc. Examples of such plant cells include cells of *Catharanthus roseus, Papaver somniferum*, etc., which can be used for the preparation of Ajima licine, cells of *Digitalis purpurea* which can be used for the preparation of β-methyldigoxin, cells of *Papaver somniferum* which can be used for the preparation of Codeine, cells of *Digitalis lanata*, cells of *Daucus carota*, cells of *Morinda citrifolia*, etc.

The animal and plant cell may be either living one or dried one, or also one broken partially or completely, as far as it has an enzyme activity. Further, such cell may be in the form physically adsorbed on a water-insoluble inorganic or organic carrier or in the form admixed with such carrier.

The weight ratio of PVA to the enzyme-producing cell (dry basis) is preferably 0.3 to 10, more preferably 0.5 to 3.

As the activated carbon powder in the present invention, commercially available activated carbon powder is used. The amount of the activated carbon powder is usually within the range of 8 to 40% by weight, in relation to PVA. Too much or too less affects the mechanical strength and the incidence rate of enzyme activity of the resulting gel containing an immobilized enzyme. Therefore, the amount of the activated carbon powder is suitably selected so that the maximum strength and the maximum incidence rate of enzyme activity may be attained.

Mixing of the aqueous PVA solution, the enzyme and the activated carbon powder is effected until a uniform mixture is obtained. The mixing can be carried out usually at room temperature. For molding the resulting mixture by half-dry gelation of PVA, said mixture, which is usually liquid, is poured into a container of any desired form and left to cause the half-dry gelation. Although the container may have any desired form, such as a granule, stick, or plate which may have fine pores, etc., it is difficult to pour the liquid into a container of granular form, on an industrial scale, and so it is usually preferred to pour the mixture into a container wherein the mixture is molded in the form of stick or plate.

Next, the mixture poured into the container is dehydrated by spontaneous drying or air drying. By such dehydration, PVA is made half-dry gelated and the mixture is molded. Here, the half-dry gelation means that PVA is converted into dry gel at such a state that a suitable amount of moisture is present in the molding obtained (the moisture content is not so low as 20 to 30%). Therefore, the above dehydration step is not a step for merely reducing the amount of moisture in the mixture, but a step for converting PVA into a half-dried gel by such a reduction in the amount of moisture and, as a result, molding said mixture.

In the above dehydration step, the spontaneous drying or the air drying is effected until the moisture content of the mixture is reduced to 50% or less. When the dehydration ratio is much lower than 50%, the amount of the gel containing immobilized enzyme obtained becomes too large. Although the dehydration ratio may be considerably higher than 50%, too high a dehydration ratio is not favorable because it may cause pulverization on finely granulating the molding or loss of water-permeability which results from over-dry-gelation. It is preferred that the dehydration ratio is within the range of 50 to 80%, at the most.

The spontaneous or air drying, which is to be effected in a temperature range not causing loss of enzyme activity, is performed usually at room temperature or a temperature of 30° to 40° C. When a thermostable enzyme or a cell producing the same is immobilized, the drying may of course be carried out at a temperature higher than that mentioned above. In the case of spontaneous drying by leaving the mixture to stand at room temperature, a considerable time is required until the completion of dehydration. Therefore, it is preferably in an industrial production to remove moisture by air drying, and at the same time, cause the half-dry gelation.

The molding thus semi-dry gelated by dehydration is next brought into contact with water to obtain an immersed gel. The purpose of this step resides in letting the surface of the molding, where the moisture content is lower than the inner part, hold a suitable amount of moisture by bringing it into contact with water. Therefore, when the dehydration ratio of the above mixture is nearly 50%, the resulting molding may not be brought into contact with water as the case may be. However, the molding is usually brought into contact with water, for the purpose as described above. The contact can be effected by immersing the molding in water or by scattering water on the molding by spraying or the like. The condition for such contact is to effect it within a temperature range not causing loss of enzyme activity. Although the molding brought into contact with water increases its moisture content, it maintains a certain moisture content and so any contact with water over a long period of time is not necessary. The moisture content of immersed gel obtained is about 70 to 80%, at the most.

The immersed gel thus obtained, or the above molding before the contact with water, is free from tackiness and so can be freely granulated at the respective stage into fine granules of suitable size, if necessary. In short, the fine granulation can be effected at a stage either before or after the contact with water. However, when the granulation is effected before the contact with water, it is advantageous for preventing pulverization to carry out the granulation within such a range as the moisture content of the molding does not become too low, for example, less than 20%.

The immersed gel thus obtained is then dried to give a firm and porous gel containing immobilized enzyme. The drying is effected usually by spontaneous drying or air drying. Since the drying has to be effected within a temperature range not causing loss of enzyme activity, it is usually carried out under temperature condition of room temperature or 30° to 40° C. Needless to say, a higher temperature may be employed for the immobilization of a thermostable enzyme or a cell producing it.

The gel containing immobilized enzyme, thus obtained, has characteristics advantageous for industrial use as an immobilized enzyme or cell for enzyme reactions, e.g., the immobilized enzymes or cells having a high mechanical strength and are tolerant of industrial use by virtue of the firm gelation proceeding from the dry gelation of PVA by spontaneous drying or air drying. Moreover, the gels are excellent in their high incidence rate of enzyme activity. Further, gels are porous and have excellent water-permeability. These properties of the gels containing an immobilized enzyme are considered to come from their structure which enables the substrate in enzyme reactions to flow well by virtue of the increased contact area among PVA, activated carbon and the enzyme, which in turn results from the possible uneven thin-layer formation by PVA on the gel containing an immobilized enzyme due to the presence of the activated carbon powder, the possible existence of the activated carbon powder inside the enzyme, and the possible immersion of PVA into the pores of activated carbon. Further, the gels containing an immobilized enzyme of the present invention have characteristics adantageous for industrial use in that their specific volume is smaller than that of immobilized cells obtained by the known freezing, molding and freeze-drying process by about ⅓ to 1/5. This enables one to reduce the volume of the reactors for enzyme reactions. Furthermore, the gels containing an immobilized enzyme can be produced on an industrial scale in safety and at low cost, according to the process of the present invention, in that the process does not require any freeze-drying step. As a result, not only the costs for equipment and energy for the freeze-drying can be saved, but also the use of harmful reagents can be avoided.

Thus, with the gels containing immobilized enzyme of the present invention, industrially useful products can be obtained by various enzyme reactions. For example, they are used for the production of 6-aminopenicillanic acid from penicillin G by means of the gels containing immobilized penicillin acylase or a microbial cell producing it, the production of isomerized sugar from glucose by means of the gel containing an immobilized glucose isomerase or a microbial cell producing it (e.g., Streptomyces albus YT-No. 5 (ATCC No. 21132, FERM-P No. 463), Streptomyces wedmorensis YT No. 4 (ATCC No. 21230, FERM-P No. 462)); the production of L-aspartic acid from fumaric acid and ammonia by means of the gel containing an immobilized aspartase or a microbial cell producing it; the production of L-phenylalanine from cinnamic acid and ammonia by means of the gel containing an immobilized L-phenylalanine ammonia lyase or a microbial cell producing it; the production of malic acid from fumaric acid by means of the gel containing immobilized fumarase or a microbial cell producing it; the production of aspartame from L-phenylalanine methyl ester and L-aspartic acid by means of the gel containing an immobilized enzyme synthesizing apartame from L-phenylalanine methyl ester and L-aspartic acid or a microbial cell producing the enzyme; the production of 7-aminocephalosporanic acid from 7-(4-carboxybutanamido)cephalosporanic acid by means of the gel containing immobilized cephalosporin acylase or a microbial cell producing it, and so on.

Streptomyces albus YT-No. 5 (ATCC No. 21132) is recited in U.S. Pat. No. 3,616,221 as an example of the glucose isomerase-producing microorganism strain and is described as forming spores which are spiny. According to the description of Inter. J. System. Bacteriol., 19: 401–403 (1969), however, it is reported that the surface of spores of Streptomyces albus strains is smooth. This discrepancy suggests there could be the possibility that some confusion might have crept into the identification of the strain. Therefore, bacteriological characteristics of the strain ATCC No. 21132 and in addition the strain ATCC No. 21230 were reexamined in order to obtain correct identification of these strains.

A. YT-No. 5 (ATCC No. 21132)

The strain YT-No. 5 (ATCC No. 21132) has the following characteristics and morphologies.

(1) Morphological Characteristics

Observation of the strain incubated at 28° C. for 10 to 14 days on an inorganic salts-starch-agar medium (ISP medium 4) described in Inter. J. System. Bacteriol., 16: 313–340 (1966) was as follows.

Substrate mycelium (0.4 to 0.5 μm is diameter) produce a flexuous branched mycelium that does not fragment readily nor produce spores. Aerial mycelium (0.4 to 0.6 μm in diameter) produced by substrate mycelium is flexuous and extends with simple branching and forms chains of many spores. The spore chain is in the form of loose spirals (usually 4 to 6 turns). The spores are spherical to ellipsoidal (0.4 to 0.6 μm × 0.6 to 0.8 μm). Observation using a transmission electron micrograph reveals that the surface of the spore is spiny. No flagellate spore nor sporangium is observed.

(2) Diaminopimelic Acid Composition

Analysis of the cell wall composition according to the method of Becker et al (Appl. Microbiol., 12: 421–423 (1964)) revealed presence of LL-type diaminopimelic acid.

(3) Growth on Various Media

Observation of the strain incubated on various media at 28° C. for 20 days was as shown in Table 1 below. Color indication was according to Color Harmony Manual 4th ed. (1958) Container Corporation of America.

TABLE 1

| Medium | Growth | Color of Substrate Mycelium | Color of Aerial Mycelium | Soluble Pigment Formation |
| --- | --- | --- | --- | --- |
| Sucrose Nitrate Agar | Moderate | Honey Gold (2 ic)–Bamboo (2 gc) | Poor; Light Beige (3 ec)–Beige (3 ge) | None |
| Glucose Asparagine Agar | Poor | Colorless | Poor-Trace; White (a) | None |
| Glycerol Asparagine | Moderate | Mustard Gold (2 pg) | Trace-Poor; Natural | None |

TABLE 1-continued

| Medium | Growth | Color of Substrate Mycelium | Color of Aerial Mycelium | Soluble Pigment Formation |
|---|---|---|---|---|
| Agar Inorganic Salts Starch Agar | Good | Golden Brown (3 pg) | (3 dc) Moderate; Beige (3 ge)–Silver Gray (3 fe) | None |
| Tyrosin Agar | Good | Golden Brown (3 pg–3 pi) | Moderate; Beige (3 ge)–Silver Gray (3 fe) | None |
| Oatmeal Agar | Moderate | Honey Gold (2 ic)–Mustard Gold (2 pg) | Poor–Moderate; Beige (3 ge)–Silver Gray (3 fe) | |
| Yeast Extract Malt Extract Agar | Good | Golden Brown (3 pg) | Moderate; Beige (3 ge)–Silver Gray (3 fe) | None |
| Nutrient Agar | Moderate | Honey Gold (2 ic) | Poor; White (a) | None |
| Bennett's Agar | Moderate–Good | Mustard Gold (2 pe) | Poor; White (a)–Beige (3 ge) | None |
| Emerson's Agar | Good | Honey Gold (2 ic) | Poor; White (a) | None |

(4) Physiological Characteristics
(1) Growth temperature: 15° to 40° C.
(2) Liquefaction of gelatin: +
(3) Hydrolysis of starch: +
(4) Peptonization of skimmed milk: +Coagulation of skimmed milk: +
(5) Melanin formation: —(ISP medium 6 or 7)
(6) Carbohydrate ultilization:
  L-Arabinose: +
  D-Fructose: +
  D-Glucose: +
  Inositol: +
  D-Mannitol: +
  L-Rhamnose: +
  Sucrose: +
  D-Xylose: +
  Raffinose: —

From the above bacteriological characteristics, more particularly, from the facts that the strain YT-No. 5 has true substrate mycelium which produce aerial mycelium bearing many spore chains, contain LL-type diamonopimelic amino acid in the cell wall, and forms no flagellate spore nor sporangium, this strain is identified as belonging to the genus Streptomyces.

Further, in view of the characteristics of the strain YT-No. 5 that the spore chain is spiral, the surface of the spore is spiny, the color of the aerial mycelium is beige to brownish gray, the color of the substrate mycelium is yellow to yellowish brown, the strain forms no soluble pigment nor melanin pigment, and the strain utilizes all the sugars tested but raffinose, extensive search was made and it was found that the above-described characteristics well coincide with those of Streptomyces rubiginosus (Preobrazhenskaya et al) Pridham et al 1958 described in Inter. J. System. Bacteriol., 18: 374 (1966).

From the foregoing, this strain was identified to be a strain belonging to Streptomyces rubiginosus.

B. YT-No. 4 (ATCC No. 21230)

The strain YT-No. 4 (ATCC No. 21230) has the following bacteriological characteristics.

(1) Morphological Characteristics

Observation of the strain incubated at 28° C. for 10 to 14 days on an inorganic salts-starch-agar medium (ISP medium 4) described in Inter. J. System. Bacteriol., 16: 313–340 (1966) was as follows.

Substrate mycelium (0.4 to 0.5 μm in diameter) produce a flexuous branched mycelium that does not fragment readily nor produce spores. Aerial mycelium (0.4 to 0.6 μm in diameter) produced by substrate mycelium is flexuous and extends with simple branching and forms chains of many spores. The spore chain is in the form of loose spirals (usually 2 to 3 turns). The spores are spherical to ellipsoidal (0.4 to 0.6 μm × 0.6 to 0.8 μm). Observation using a transmission electron micrograph reveals that the surface of the spore is spiny. No flagellate spore nor sporangium is observed.

(2) Diaminopimelic Acid Composition

Analysis of the cell wall composition according to the method of Becker et al (Appl. Microbiol., 12: 421–423 (1964)) revealed presence of LL-type diaminopimelic acid.

(3) Growth on Various Media

Observation of the strain incubated on various media at 28° C. for 20 days was as shown in Table 2 below. Color indication was according to Color Harmony Manual 4th ed. (1958) Container Corporation of America.

TABLE 2

| Medium | Growth | Color of Substrate Mycelium | Color of Aerial Mycelium | Soluble Pigment Formation |
|---|---|---|---|---|
| Sucrose Nitrate Agar | Moderate | Bamboo (2 gc) | Poor; Light Beige (3 ec)–Beige (3 ge) | None |
| Glucose Asparagine Agar | Poor | Colorless | None–Trace; White (a) | None |
| Glycerol Asparagine Agar | Moderate–Good | Beaver (3 li) | Moderate; Light Beige (3 ec)–Beige (3 ge) | None |
| Inorganic Salts Starch Agar | Good | Golden Brown (3 pg–3 pi) | Good; Beige (3 ge)–Beige Brown (3 ig) | None |
| Tyrosin Agar | Good | Golden Brown (3 pg–3 pi) | Good; Beige (3 ge)–Beige Brown (3 ig) | None |
| Oatmeal Agar | Moderate | Bamboo (2 gc) | Moderate; Light Beige (3 ec)–Beige (3 ge) | None |
| Yeast Extract Malt Extract Agar | Good | Golden Brown (3 pg–3 pi) | Moderate; Beige (3 ge)–Beige Brown (3 ig) | None |
| Nutrient Agar | Moderate | Honey Gold (2 ic) | Poor; White (a) | None |
| Bennett's Agar | Moderate | Mustard Gold (2 pg) | Poor; Beige (3 ge)–Light Beige (3 ec) | None |

TABLE 2-continued

| Medium | Growth | Color of Substrate Mycelium | Color of Aerial Mycelium | Soluble Pigment Formation |
|---|---|---|---|---|
| Emerson's Agar | Good | Honey Gold (2 ic) | Poor; White (a)–Light Beige (3 ec) | None |

(4) Physiological Characteristics
(1) Growth temperature: 15° to 40° C.
(2) Liquefaction of gelatin: +
(3) Hydrolysis of starch: +
(4) Peptonization of skimmed milk: +Coagulation of skimmed milk: +
(5) Melanin formation: −(ISP medium 6 or 7)
(6) Carbohydrate ultilization:
  L-Arabinose: +
  D-Fructose: +
  D-Glucose: +
  Inositol: +
  D-Mannitol: +
  L-Rhamnose: +
  Sucrose: +
  D-Xylose: +
  Raffinose: −

From the above bacteriological characteristics, more particularly, from the fact that the strain YT-No. 4 has true substrate mycelium which produce aerial mycelium bearing many spore chains, contain LL-type diaminopimelic acid in the cell wall, and forms no flagellate spore nor sporangium, this strain is identified as belonging to the genus Streptomyces.

Further, in view of the characteristics of the strain YT-No. 4 that the spore chain is spiral, the surface of the spore is spiny, the color of the aerial mycelium is beige to brownish gray, the color of the substrate mycelium is yellow to yellowish brown, the strain forms no soluble pigment nor melanin pigment, and the strain utilizes all the sugars tested but raffinose, extensive search was made.

As a result, it was found that the strain YT-No. 4 does not belong to *Streptomyces wedmorensis* since this strain forms a spiral spore chain in contrast to *Streptomyces wedmorensis* which forms a straight spore chain according to Waksman, S. A.; The Actinomycetes vol. 2, 290 (1961), The Williams & Wilkinson Co. and it was found that the above-described characteristics well coincide with those of *Streptomyces rubiginosus* (Preobrazhenskaya et al) Pridham et al 1958 described in Inter. J. System. Bacteriol., 18: 374 (1966).

From the foregoing, this strain was identified to be a strain belong to *Streptomyces rubiginosus*.

The present invention is further explained in detail by giving Examples and Reference Exaples. These Examples, however, should not be construed as limitating the immobilizing process of the present invention and the enzymes or microbial cells producing them used in the present invention. It will be understood that, after disclosure of the present invention, any enzyme or any microbial cell producing it, which is not disclosed in Examples, can also be immobilized easily.

The strength and the incidence rate of the activity of immobilized microbial cells were determined according to the followng methods, unless otherwise described specifically.

Method of Strength Test:
In a 200 ml conical flask were placed 5 g of an immobilized microbial cell to be tested and 100 ml of water, and stirred an incubator at 70° C. with a magnetic stirrer at a constant speed (about 60 r.p.m.). After 90 minutes, the degree of disintegration was evaluated by visual observation according to the following criterion.
 −: completely disintegrated
 ±: considerably disintegrated
 +: only partially disintegrated
 ++: almost not disintegrated Incidence Rate of Activity:
The specific activity of the enzyme titer of an immobilized microbial cell determined without pulverization was expressed by percentage in relation to the enzyme titer of the same immobilized microbial cell determined after complete pulverization, said complete pulverization being effected by rotation with Histocolon (made by Nihon Seimitsu Kogyo Ltd.) for 30 seconds at a graduation of 40.

EXAMPLES 1 TO 3

In a mixing container were placed 200 g of wet cells of *Streptomyces albus* YT-No. 5 (ATCC No. 21132, FERM-P No. 463) producing glucose isomerase (dry weight 46 g, obtained by cultivation according to the process described in Japanese Patent Application (OPI) No. 7480/77), 300 g of water and 5 g (Example 1), 10 g (Example 2) or 20 g (Example 3) of activated carbon powder (Shirasagi A). After mixing uniformly, 240 g of 20% aqueous PVA solution (a solution of 48 g of a commercially available PVA having a saponification degree of 99.45 mol% and a polymerization degree of 1,700 in 192 g of water) was added and further mixed uniformly. Into a groove for molding of 2×2 mm square and 20 cm length was poured 14.0 g of each mixture obtained above, with an injector, and then the mixture was air-dried at 45° C. for 3.5 hours. Each molding thus obtained was immersed in water and then cut into 2 mm cubes. The cubes were air-dried at 50° C. for 16 hours to give immobilized microbial cells. The strength and the incidence rate of the activity of each of the immobilized cells thus obtained are shown in Table 3.

REFERENCE EXAMPLE 1

In a mixing container were placed 200 g of wet cells of *Streptomyces albus* YT-No. 5 (ATCC No. 21132) and 300 g of water. To the suspension thus obtained was added 240 g of 20% aqueous PVA solution, and the mixture was mixed uniformly. In the same manner as Example 1, 14.0 g of the mixture was poured into a groove for molding and air-dried at 45° C. for 10 hours to give a stick of immobilized cells.The stick was cut into 2 mm cubes to give granular immoblized cells (moisture content 22%), whose strength and activity incidence rate were those shown in Table 3.

REFERENCE EXAMPLE 2

In a mixing container were placed 200 g of wet cells of *Streptomyces albus* YT-No. 5 (ATCC No. 21132) and 300 g of water. To the suspension thus obtained was added 240 g of 20% aqueous PVA solution, and the mixture was mixed uniformly. In the same manner as Example 1, 14.0 g of the mixture was poured into a groove for molding and frozen at −20° C. for 8 hours. Then, the frozen molding was dried under vacuum for 16 hours to give a stick of immobilized cells. The stick was cut into 12 mm cubes to give granular immobilized cells, whose strength and activity incidence rate were those shown in Table 3.

REFERENCE EXAMPLE 3

In a mixing container were placed 200 g of wet cells of Streptomyces albus YT-No. 5 (ATCC No. 21132), 300 g of water and 10 g of activated carbon powder (Shirasagi A). The mixture was mixed uniformly. Then, 240 g of 20% aqueous PVA solution was added to the mixture and mixed further uniformly. In the same manner as Example 1, 14.0 g of the mixture was poured into a groove for molding and air-dried at 45° C. for 3.5 hours to give a molding. The molding was immersed in water, cut into 2 mm cubes, and then frozen at −20° C. for 8 hours. By drying the frozen cubes under vacuum for 16 hours, immobilized microbial cell was obtained. The strength and the activity incidence rate of the immobilized cells are shown in Table 3.

TABLE 3

| Immobilized Cell | Amount of Activated Carbon Added (g) | Strength | Incidence Rate of Activity (%) |
|---|---|---|---|
| Example 1 | 5 | + | 85 |
| Example 2 | 10 | ++ | 90 |
| Example 3 | 20 | + | 85 |
| Reference Example 1 | — | — | 92 |
| Reference Example 2 | — | ± | 85 |
| Reference Example 3 | 10 | ± | 85 |

The above results indicate that the immobilized cell of Reference Example 1 cannot be used for industrial production because of its very low mechanical strength, although it has a high incidence rate of activity. Further, the immobilized cell of Reference Example 2 has a volume of about 3 times as large as the immobilized cell of the present invention and accordingly induces significant expansion of reactors when it is utilized for industrial enzyme reactions, although it has some mechanical strength. The immobilized cell of Reference Example 3, which is obtained by adding activated carbon and by the combined use of the half-dry gelation and the low temperature gelation, is inferior in mechanical strength compared with the immobilized cell of the present invention.

EXAMPLES 4 TO 6

In a mixing container were placed 200 g of wet cells of Streptomyces YT-No. 4 (ATCC No. 21230, FERM-P No. 462) producing glucose isomerase (dry weight 46 g, obtained by cultivation according to the process described in Japanese Patent Application (OPI) No. 7480/77), 300 g of water and 5 g (Example 4), 10 g (Example 5) or 20 g (Example 6) of activated carbon powder (Shirasagi A). After mixing uniformly, 240 g of 20% aqueous PVA solution (a solution of 48 g of a commercially available PVA having a saponification degree of 99.45 mol% and a polymerization degree of 1,700 in 192 g of water) was added and further mixed uniformly. Into a groove for molding of 2×2 mm square and 20 cm length was poured 14.0 g of each mixture obtained above, with an injector, and then the mixture was air-dried at 45° C. for 3.5 hours. Each molding thus obtained was immersed in water and then cut into 2 mm cubes. The cubes were air-dried at 50° C. for 16 hours to give immobilized microbial cells. The strength and the incidence rate of the activity of each of the immobilized cells thus obtained are shown in Table 4.

REFERENCE EXAMPLE 4

In a mixing container were placed 200 g of wet cells of Streptomyces YT-No. 4 (ATCC No. 21230) and 300 g of water. To the suspension thus obtgained was added 240 g of 20% aqueous PVA solution, and the mixture was mixed uniformly. In the same manner as Example 4, 14.0 g of the mixture was poured into a groove for molding and air-dried at 45° C. for 10 hours to give a stick of immobilized cells. The stick was cut into 2 mm cubes to give granular immobilized cells (moisture content 22%), whose stgrength and activity incidence rate were those shown in Table 4.

REFERENCE EXAMPLE 5

In a mixing contgainer were placed 200 g of wet cells of Streptomyces YT-No. 4 (ATCC No. 21230 and 300 g of water. To the suspension thus obtained was added 240 g of 20% aqueous PVA solution, and the mixture was mixed uniformly. In the same manner as Example 4, 14.0 g of the mixture was poured into a groove for molding and frozen at −20° C. for 8 hours. Then, the frozen molding was dried under vacuum for 16 hours to give a stick of immobilized cells. The stick was cut-into 12 mm cubes to give granular immobilized cells, whose strength and activity incidence rate were those shown in Table 4.

REFERENCE EXAMPLE 6

In a mixing container were placed 200 g of wet cells of Streptomyces YT-No. 4 (ATCC No. 21132), 300 g of water and 10 g of activated carbon powder (Shirasagi A). The mixture was mixed uniformly. Then, 240 g of 20% aqueous PVA solution was added to the mixture and mixed further uniformly. In the same manner as Example 4, 14.0 g of the mixture was poured into a groove for molding and air-dried at 45° C. for 3.5 hours to give a molding. The molding was immersed in water, cut into 2 mm cubes, and then frozen at −20° C. for 8 hours. By drying the frozen cubes under vacuum for 16 hours, immobilized microbial cell was obtained. The strength and the activity incidence rate of the immobilized cells are shown in Table 4.

TABLE 4

| Immobilized Cell | Amount of Activated Carbon Added (g) | Strength | Incidence Rate of Activity (%) |
|---|---|---|---|
| Example 4 | 5 | + | 86 |
| Example 5 | 10 | ++ | 89 |
| Example 6 | 20 | + | 85 |
| Reference Example 4 | — | — | 94 |
| Reference Example 5 | — | ± | 86 |
| Reference Example 6 | 10 | ± | 84 |

The above results indicate that the immobilized cell of Reference Example 4 cannot be used for industrial production because of its very low mechanical strength, although it has a high incidence rate of activity. Further, the immobilized cell of Reference Example 5 has a volume of about 3 times as large as the immobilized cell of the present invention and accordingly induces significant expansion of reactors when it is utilized for industrial enzyme reactions, although it has some mechanical strength. The immobilized cell of Reference Example 6, which is obtained by adding activated carbon and by the combined use of the half-dry gelation and the low temperature gelation, is inferior in mechanical strength compared with the immobilized cell of the present invention.

EXAMPLE 7

100 mg of commercially available glucose oxidase (Toyobo Co., Ltd., 116 U/mg) and 100 mg of commercially available catalase (Sigma, 3100 Sigma U/mg) were dissolved in 500 ml of an acetate buffer (pH 5.0). 23 g of activated carbon (Shirasagi A) was added to the resulting enzyme solution, and the mixture was stirred for 1 hour. After filtration, immobilized enzyme preparation comprising glucose oxidase and catalase adsorbed on activated carbon was obtained. The endzyme preparation had a glucose oxidase activity of 6 U/g. To the entire amount of the immobilized enzyme preparation was added 450 ml of a 20% aqueous PVA solution (a solution of 48 g of a commercially available PVA having a saponification degree of 99.45 mol% and a polymerization degree of 1,700 in 192 g of water) was added and further mixed uniformly. Into a groove for molding of 2×2 cm square and 20 cm length was poured 14.0 g of the mixture obtained above, with an injector, and then the mixture was air-dried at 45° C. for 3.5 hours. The molding thus obtained was immersed in water and then cut into 2 mm cubes. The cubes were air-dried at 50° C. for 16 hours to give immobilized enzyme preparation. The glucose oxidase activity of the immobilized enzyme preparation thus obtained was 6 U/g.

While the invention has been described in detail and with reference to specific embodiments thereof, it will be apparent to one skilled in the art that various changes and modifications can be made therein without departing from the spirit and scope thereof.

What is claimed is:

1. A process for the preparation of a porous gel containing an immobilized enzyme or enzyme-producing cell, comprising:
   (A) mixing (i) a 5 to 30 w/w% aqueous solution of polyvinyl alcohol having a saponification degree of not lower than 95 mol% and an average polymerization degree of not lower than 1,000, with (ii) an enzyme or enzyme-producing cell, and (iii) activated carbon powder in an amount of 8 to 40% by weight based on the polyvinyl alcohol;
   (B) pouring the resulting mixture into a container of any desired form;
   (C) dehydrating the mixture by leaving the mixture to stand at room temperature or a temperature of from 30° C. to 40° C. in the container up to a dehydration ratio of not lower than 50% to gelate the mixture in the container whereby the resulting gel has the form of the container;
   (D) immersing the resulting gel in water, and
   (E) removing the gel from the water and drying the gel.

2. The process as claimed in claim 1, wherein said enzyme-producing cell is an enzyme-producing microbial cell.

3. The process as claimed in claim 2, wherein the enzyme or enzyme-producing microbial cell is in admixture with an inorganic or organic carrier, or is adsorbed on an inorganic or organic carrier.

4. The process as claimed in claim 3, wherein said enzyme or enzyme-producing microbial cell and said inorganic or organic carrier are in suspension.

5. The process as claimed in claim 3, wherein the enzyme or enzyme-producing microbial cell is in the form of a solution or suspension in an aqueous medium.

6. The process as claimed in claim 5, wherein said enzyme or enzyme-producing microbial cell and said inorganic or organic carrier are in suspension.

7. The process as claimed in claim 2, wherein the enzyme-producing microbial cell is selected from the group consisting of a living cell, a dried cell, and a broken cell.

8. The process as claimed in claim 2, wherein the container is one adapted to form sticks or plates of the gel.

9. The process as claimed in claim 2, wherein step (D) is carried out under conditions within a temperature range that does not cause the loss of enzyme activity.

10. The process as claimed in claim 7, wherein the resulting sticks or plates after drying are finely granulated.

11. The process as claimed in claim 2, wherein the drying is carried out by leaving the mixture to stand at room temperature or a temperature of from 30° to 40° C.

12. The process as claimed in claim 7, wherein said enzyme-producing microbial cell is in admixture with an inorganic or organic carrier or is adsorbed on an inorganic or organic carrier.

* * * * *